US008835661B2

(12) United States Patent
Couturier et al.

(10) Patent No.: US 8,835,661 B2
(45) Date of Patent: Sep. 16, 2014

(54) PROCESS FOR THE SYNTHESIS OF C11 AND C12 OMEGA-AMINOALKANOIC ACID ESTERS COMPRISING A NITRILATION STEP

(75) Inventors: Jean-Luc Couturier, Lyons (FR); Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/240,886

(22) PCT Filed: Jul. 26, 2012

(86) PCT No.: PCT/FR2012/051771
§ 371 (c)(1),
(2), (4) Date: Feb. 25, 2014

(87) PCT Pub. No.: WO2013/030481
PCT Pub. Date: Mar. 7, 2013

(65) Prior Publication Data
US 2014/0200358 A1    Jul. 17, 2014

(30) Foreign Application Priority Data
Aug. 26, 2011   (FR) .................................... 11 57542

(51) Int. Cl.
*C07C 233/00* (2006.01)
*C07C 227/06* (2006.01)

(52) U.S. Cl.
CPC .................................. *C07C 227/06* (2013.01)
USPC ......................................................... 554/69

(58) Field of Classification Search
CPC ................................................... C07C 233/00
USPC ........................................................ 554/69
See application file for complete search history.

(56) References Cited

U.S. PATENT DOCUMENTS

| 4,801,730 A | 1/1989 | Stuehler et al. |
| 6,005,134 A | 12/1999 | Terasaka et al. |
| 6,080,891 A | 6/2000 | Terasaka et al. |
| 7,259,274 B2 | 8/2007 | Terasaka et al. |
| 2011/0224454 A1 | 9/2011 | Dubois |

FOREIGN PATENT DOCUMENTS

| JP | H04-208260 A | 7/1992 |
| JP | H04-283549 A | 10/1992 |
| JP | H10-195035 A | 7/1998 |
| JP | 2000-016977 A | 1/2000 |
| WO | WO 2010/055273 A1 | 5/2010 |
| WO | WO 2010055273 A1 * | 5/2010 ............ C07C 229/08 |

OTHER PUBLICATIONS

International Search Report (PCT/ISA/210) mailed on Nov. 21, 2012, by the French Patent Office as the International Searching Authority for International Application No. PCT/FR2012/051771.
Aharoni, "n-Nylons, Their Synthesis, Structure and Properties", 1997 (month unknown), pp. 380-389, Section 2.9 "Specifics of the n-Nylons", published by J. Wiley and Sons.
Chauvel et al., "Les Procédés de Pétrochimie—Caractéristiques techniques et économiques", 1986 (month unknown), pp. 316-323, published by Editions TECHNIP.
Mol, "Catalytic metathesis of unsaturated fatty acid esters and oil", Topics in Catalysis, Feb. 2004, pp. 97-104, vol. 27, Nos. 1-4, published by Plenum.
Schaverien et al., "A Well-Characterized, Highly Active, Lewis Acid Free Olefin Metathesis Catalyst", Journal of Am. Chem. Soc., 1986 (month unknown), pp. 27771-2773, vol. 108.
Couturier et al., "A Cyclometalated Aryloxy(chloro)neopentylidene-tungsten Complex: A Highly Active and Stereoselective Catalyst for the Metathesis of eis- and trans-2-Pentene, Norbornene, 1-Methynorbornene, and Ethyl Oleate", Angew. Chem., Ed. Engl., Jul. 1992, pp. 628-631, vol. 31, No. 5.
Schwab et al., "A Series of Well-Defined Metathesis Catalysts-Synthesis of [RuCl2(=CHR')(PR3)2I and its Reactions", Angew. Chem., Ed. Engl., 1995 (month unknown), pp. 2039-2041, vol. 34, No. 18.
Scholl et al., "Synthesis and Activity of a New Generation of Ruthenium-Based Olefin Metathesis Catalysts Coordinated with 1,3-Dimesityl-4,5-dihydroimidazol-2-ylidene Ligands", Organic Letters, Aug. 1999, pp. 953-956, vol. 1, No. 6.
Perkins, Jr et al., "Nylon-9 from Unsaturated Fatty Derivatives: Preparation and Characterization", Journal of the American Oil Chemists Society, Nov. 1975, pp. 473-477, vol. 52, issue 11.
Pryde et al., "Aldehydic Materials by the Ozonization of Vegetable Oils", The Journal of the American Oil Chemists Society, Nov. 1962, pp. 496-500, vol. 39, issue 11.
Throckmorton, "Pilot Run, Plant Design and Cost Analysis for Reductive Ozonolysis of Methyl Soyate", The Journal of the American Oil Chemists Society, Nov. 1972, pp. 643-648, vol. 49, issue 11.

* cited by examiner

*Primary Examiner* — Deborah D Carr
(74) *Attorney, Agent, or Firm* — Buchanan Ingersoll & Rooney P.C.

(57) ABSTRACT

A process for the synthesis of C11 and C12 ω-amino-alkanoic acid esters including a step of continuous nitrilation in the gas phase or in a mixed gas-liquid phase, a step of metathesis and a step of reduction by hydrogenation, using, as raw material, C10 and C11 ω-alkenoic acid esters.

13 Claims, No Drawings

PROCESS FOR THE SYNTHESIS OF C11 AND C12 OMEGA-AMINOALKANOIC ACID ESTERS COMPRISING A NITRILATION STEP

STATEMENT

The work leading to this disclosure received financing from the European Union as part of Framework Programme 7 (FP7/2007-2013) under project number 241718 EURO-BIOREF.

TECHNICAL FIELD

Embodiments of the disclosure are directed to a process for synthesizing esters of C11 and C12 ω-aminoalkanoic acids, comprises a step of metathesis, using esters of C10 and C11 ω-alkenenoic acids as starting material.

BACKGROUND SUMMARY

The polyamides industry uses a whole range of monomers consisting of long-chain ω-amino acids, commonly termed Nylon, which are characterized by the length of methylene chain $(-CH_2)_n$ separating two amide functions -CO—NH—. Known, accordingly, are nylon 6, nylon 6-6, nylon 6-10, nylon 7, nylon 8, nylon 9, nylon 11, and nylon 13, etc. The "higher" nylons 11 and 13, for example, which use ω-amino acids as monomer, occupy a separate place in this class, insofar as they are synthesized not from petroleum-derived products (C2 to C4 olefins, cycloalkanes or benzene), but from fatty acids/esters which are present in natural oils.

One example of a process using a fatty acid as starting material is that of the preparation of fatty nitriles and/or amines from fatty acids extracted from plant or animal oils. This process is described in the Kirk-Othmer encyclopedia, vol. 2, 4th edition, page 411. The fatty amine is obtained in a number of steps. The first step involves methanolysis or hydrolysis of a plant oil or of an animal fat, producing, respectively, the methyl ester of a fatty acid, or a fatty acid. The methyl ester of the fatty acid may subsequently be hydrolyzed to form the fatty acid. The fatty acid is subsequently converted into nitrile by reaction with ammonia, and finally into amine by hydrogenation of the resultant nitrile.

Within the field of chemistry, moreover, present environmental developments are resulting in preference being given to the exploitation of natural raw materials originating from a renewable source. It is for this reason that certain research and development studies have been taken up for the purpose of industrial development of processes using fatty acids/esters as starting material for preparation of these ω-amino acid monomers.

The main studies have looked at the synthesis of 9-amino nonanoic acid, the precursor to Nylon 9, from oleic acid of natural origin. With regard to this monomer, it is possible to cite the work "n-Nylons, Their Synthesis, Structure and Properties"-1997, published by J. Wiley and Sons, in which section 2.9 (pages 381 to 389) is devoted to 9-Nylon.

Industrially, for the preparation of polyamide polymerization monomers, there are only few examples of processes using natural oils as starting material. One of the rare examples of an industrial process using a fatty acid as starting material is the preparation process, from the methyl ester of ricinoleic acid, extracted from castor oil, of 11-amino undecanoic acid, which forms the basis for the synthesis of Rilsan 11®. This process is described in the work "Les Procédés de Pétrochimie" by A. Chauvel et al., published by Editions TECHNIP (1986). The 11-amino undecanoic acid is obtained in a number of steps. The first involves a methanolysis of the castor oil in a basic medium, producing methyl ricinoleate, which is subsequently subjected to pyrolysis to give heptanaldehyde on the one hand and methyl undecylenate on the other. The latter is converted into acid form by hydrolysis. The acid formed is subsequently subjected to hydrobromination, to give the ω-brominated acid, which is converted by ammonolysis into 11-amino undecanoic acid.

The applicant has since continued work on the processes for synthesis of these higher monomers, based on the use of natural oils which are sources of oleic, ricinoleic, lesquerolic, erucic or other acids. The applicant, accordingly, has explored a pathway wherein the acid function was converted during the process into nitrile function by nitrilation (ammonization) and then, after introduction of an acid or ester function into the molecule, by oxidative cleavage or metathesis with an acrylate, was reduced to primary amine function at the end of the conversions. This is the context in which the applicant filed a patent application, WO2010/055273, covering different versions of implementation of the process, all of them involving the formation of an ω-unsaturated fatty nitrile.

SUMMARY OF THE DISCLOSURE

In the process of embodiments of the disclosure, one step is the nitrilation of the acid/ester function of the unsaturated fatty acid.

The reaction scheme for the synthesis of nitriles from a fatty acid may be summarized as follows.

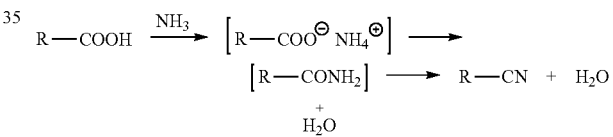

There are two types of processes based on this reaction scheme: a (generally batch) process in liquid phase, and a (generally continuous) process in vapor phase.

In the batch process (liquid phase), the fatty acid or a mixture of fatty acids is charged with a catalyst, which is generally a metal oxide and usually zinc oxide. The reaction mixture is brought to approximately 150° C. with stirring, and then the introduction of gaseous ammonia is commenced. In a first phase, an ammonium salt or ammonium soap is formed. The temperature of the reaction mixture is then brought to around 250°-300° C., still with introduction of ammonia. The ammonium salt undergoes conversion to amide, with release of a first molecule of water. Then, in a second phase and with the aid of the catalyst, the amide undergoes conversion into nitrile, with formation of a second molecule of water. This water formed is removed continuously from the reactor, carrying with it the unreacted ammonia and a small amount of the lighter fatty chains.

In the (continuous) gas-phase process, the charge is evaporated and brought into contact with ammonia which is at a temperature of between 250 and 600° C., in the presence of a catalyst. This catalyst is generally selected from the class of metal oxides consisting of the oxides of metals, taken alone or as a mixture, such as Zr, Ta, Ga, In, Sc, Nb, Hf, Fe, Zn, Sn or alumina, silica, a thorium oxide, and particularly doped alumina.

These reactions, in their various forms, are mentioned in the Ullmann encyclopedia, vol. A2, page 20, and the Kirk Othmer encyclopedia, vol. 2, pages 411-412, and have been a subject of numerous patents, filed in particular by the company KAO. These include U.S. Pat. Nos. 6,005,134, 6,080, 891, and 7,259,274, which describe the synthesis of aliphatic nitriles in liquid phase from fatty acids in the presence of a titanium catalyst. For the same applicant and for the same type of process, there are Japanese applications 11-117990 (26 Apr. 1999) with a niobium catalyst, and 9-4965 (14 Jan. 1997) with a zirconium catalyst. There is also a U.S. Pat. No. 4,801,730, which describes the nitrilation of glycerides in liquid phase, and a Japanese application in the name of Lion Corp, of Mar. 13, 1991 (publication No. JP 4283549), which is directed to the synthesis of nitrile in gaseous phase.

In the studies it has conducted, the applicant has observed that the nitrilation step played an important part, particularly in view of the fact that it was carried out on an ω-unsaturated acid. The reason is that the location of the double bond at the chain end, and therefore with little protection, is able to give rise to formation of isomers, owing to the shifting of the double bond. Having observed these phenomena, the applicant noted that this drawback could be largely limited by working with the ester rather than with the corresponding acid, which would allow operation under "milder" conditions. The reason is that, since the boiling point of the ester was lower than that of the corresponding acid, it was possible to obtain stronger vapor tensions with the ester. Moreover, by working in a reactor operating continuously either in gas phase or in mixed liquid-gas phase, the residence time of the reactants in contact with the catalysts was significantly less than in conventional (batch) liquid phase, allowing isomerization during the process to be limited.

The known art essentially describes the liquid-phase nitrilation of the acid, and those which talk of gas phase ignore the problem of the isomerization of the terminal double bonds, their objectives being greatly different from those of the process of embodiments of the disclosure.

The process of embodiments of the disclosure aims to overcome the drawbacks of the known art.

DETAILED DESCRIPTION

Embodiments of the disclosure provide a process for synthesizing acids or esters of ω-aminoalkanoic acids comprising 11 or 12 carbon atoms from ω-unsaturated acid or ester comprising respectively 10 or 11 carbon atoms, characterized in that it comprises three main steps:
1) nitrilation of the ω-unsaturated acid/ester of the charge, of formula $CH_2=CH—(CH_2)_n—COOR$, in which n is 7 or 8 and R is either H or an alkyl radical comprising 1 to 4 carbon atoms, by action of ammonia, in a reactor operating continuously in gas phase or in mixed gas-liquid phase, in the presence of a solid catalyst, then
2) conversion of the resulting nitrile of formula $CH_2=CH—(CH_2)_n—CN$ by metathesis with an acrylate of formula $CH_2=CH—COOR_1$, where $R_1$ is either H or an alkyl radical comprising 1 to 4 carbon atoms, and lastly
3) hydrogenative reduction of the nitrile function of the compound of formula $R_1OOC—CH=CH—(CH_2)_n—CN$ to give an amino acid or an amino ester of formula $R_1OOC—(CH_2)_{n+2}—CH_2NH_2$.

The nitrilation step is carried out in a reactor operating continuously, in other words in which the reactants, whether gaseous or liquid in origin, are introduced (and the products are extracted) into (and from) the reactor continuously in accordance with predetermined flow rates.

In a first embodiment, the two reactants may be introduced into the reactor in the gaseous state (pure gaseous phase).

In the other embodiment (mixed phase), the ammonia is introduced in the form of gas while the ester (acid) is introduced, after optional preheating, into the reactor close to the catalyst bed, at least partly in liquid form at a rate determined so as to flow in the form of a film (trickle bed) over the heated catalyst bed, in contact with which a fraction of the liquid is evaporated. The reaction, or reaction series, takes place on contact with the surface of the catalyst, or in its immediate proximity. This "trickle bed" technique is well-known and widely employed in the petroleum industry. The flow of ammonia may be cocurrent or counter-current to the flow of ester.

The process of embodiments of the disclosure use as its charge ω-unsaturated acids or esters comprising either 10 atoms or 11 atoms of carbon per molecule. The first—particularly methyl 9-decenoate—are sold in ester form by ELEVANCE Renewable Sciences; the second—particularly methyl 10-undecenoate—are produced by the company ARKEMA in its aforementioned castor oil-based process, with the methyl undecylenate being obtained after pyrolysis.

The acrylate used in the second step will be selected from acrylic acid, methyl acrylate, ethyl acrylate, n-propyl or isopropyl acrylate, or n-butyl, isobutyl, sec-butyl or tert-butyl acrylate.

The reaction scheme for the process is as follows:

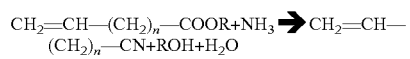

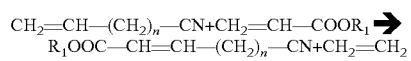

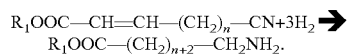

Nitrilation Step

The process of catalytic nitrilation of fatty acids is carried out at a reaction temperature of generally between 200 and 400° C. and preferably between 250 and 350° C. The ω-unsaturated fatty acids/esters charge is evaporated and brought to a temperature of between 180 and 350° C. in contact with ammonia introduced at a temperature of between 150 and 600° C.

The pressure is between 0.1 and 10 atmospheres (absolute) and preferably between 0.5 and 5, and more preferably between 1 and 3 atm.

When the nitrilation step is carried out in gas phase, the ω-unsaturated ester of fatty acids is evaporated and brought at a temperature of between 180 and 350° C. in contact with ammonia introduced at a temperature of between 150 and 600° C. and under a pressure of between 0.1 and 10 atmospheres (absolute), preferably between 0.5 and 5, and more preferably between 1 and 3 atmospheres, in the presence of solid catalyst; the reaction temperature is preferably between 200° C. and 400° C.

In the variant embodiment of the process that is entirely in gas phase, the rates at which the reactants are introduced are such that the contact time with the solid catalyst is between 1 second and 300 seconds. In this case, the contact time is determined by the ratio calculated as follows: {volume of catalyst (in liters)×3600}/{[flow rate of unsaturated ester (in moles/h)+flow rate of ammonia (in moles/h)]×22.4}=contact time in seconds.

In a variant of the process, the step of nitrilation of the ω-unsaturated fatty acid ester is carried out in mixed phase according to the trickle bed technique, the ω-unsaturated ester of fatty acids, optionally preheated, being passed progressively in trickling liquid form over the solid catalyst, which is heated at a temperature such that there is partial, progressive evaporation of the ester, allowing the reactions with ammonia on contact with the surface of the catalyst or in its immediate proximity. The reaction temperature is generally between 200 and 400° C. and preferably between 250 and 350° C. The rate at which the ester is introduced is such that the mean residence time of the liquid phase in the reactor is less than 1 hour, and preferably less than 30 minutes. This contact time is determined by the following calculation: volume of catalyst (in liters)/flow rate of unsaturated ester (in liquid liters at 25° C. per hour), or the inverse of the liquid hourly liquid volume rate.

In this embodiment, it is possible to work in cocurrent, meaning that the gas current and the liquid flow are descending, or in countercurrent, with the gas flow being ascending and the liquid flow descending. This latter variant is preferred in the process of an embodiment of the disclosure. The countercurrent version, with gas ascending and ester descending, may be of particular advantage for limiting the hydrolysis of the nitrile formed. The reason is that in this configuration, the ammonia is injected at the bottom, and the water and alcohol emerge at the top; the ester enters at the top, and the nitrile emerges at the bottom. At the bottom, therefore, the concentration of nitrile and of ammonia is high, and at the top the concentration of ester, water, and alcohol is high, and the concentration of ammonia is less. It is therefore possible to shift the equilibria, particularly that of the hydrolysis of the nitrile, which restores the acid.

The molar $NH_3$/fatty ester ratio of the reactants is between 1 and 50, preferably between 3 and 30, and more preferably between 5 and 20.

The reaction is carried out in the presence of a solid catalyst.

This catalyst is selected from the class of metal oxides or mixed metal oxides, consisting of the oxides of metals, alone or as a mixture, such as Zr, Ce, Ti, Mo, W, V, S, P, Ta, Ga, In, Sc, Nb, Hf, Fe, Zn, Sn, Al, Si. The oxides or mixed oxides constituting the catalyst may be doped with other metals for the purpose of enhancing the catalytic performance levels. The dopants which are suitable for the application include the following: rare earths, La, Pr, Nd, Sm, Eu, Dy, Gd, Ho, Yb, and also Cu, Ni, Fe, Pb, Sn, In, Mn, Co, Mo, W, Nb, Zn, Cr, Si, Mg, Ca, Sr, Sc, Y.

Preferred catalysts in the process of embodiments of the disclosure are oxides based on zirconium, on cerium, on titanium, on niobium, or on aluminum.

With zirconium oxide, the dopant used will comprise rare earths, in an amount of 5 to 50 mol %, and preferably from 8% to 15%, but also P, S, Cu, Ni, Fe, Pb, Sn, In, Mn, Mo, W, Nb, Zn, Cr, Si with amount of 1% to 30% and preferably greater than 5%.

With cerium oxide, the dopant used will preferably be as follows: Mg, Ca, Sr, Sc, Y, and rare earths, with amounts of 1% to 50%, and preferably more than 10%.

With titanium oxide, the dopant preferred will be W, Mo, P, S, Fe, Nb, Sn, Si, with amounts of 1% to 50% and preferably of 5% to 20%.

As a method for preparing the catalysts, there are a number of possible candidate methods, including coprecipitation, atomization, mixing, and impregnation. Precursors of the oxides in various forms may be used, particularly in oxide, nitrate, carbonate, chloride, sulfate (including oxysulfate), phosphate, organometallic compound, acetate, and acetylacetonate form. It is also possible to use the salts in sulfate or phosphate form in the preparation of catalysts insofar as S or P are used as dopants of the catalyst. In that case, the preparation of a catalyst from zirconium or titanium oxysulfate leads to a catalyst suitable for the process of embodiments of the disclosure.

The catalysts have a specific surface area of between 10 and 500 $m^2$/g, and preferably of between 40 and 300 $m^2$/g.

The catalysts are formed by techniques which are suitable according to the type of reactor used.

A number of reactor technologies may be suitable for the process of embodiments of the disclosure: fixed bed reactors, fluidized bed reactors in gas phase.

For the fixed bed reactors, the catalysts are present in the form of particles with a particle size of 1 to 10 mm, or in the form of porous monoliths. The catalyst may in that case have a variety of forms: beads, cylinders—hollow or not—sticks, etc. The reactor is used either solely in gas phase or else as a trickle bed, where a gas phase coexists with a liquid phase.

The reactor may be employed as a fluidized bed. In this case, the catalyst is preset in the form of a powder with a diameter of 40 to 500 microns and preferably with an average particle size of 80 to 250 microns. The gas flow rate of $NH_3$ reactant (majority gas in the reactor) is sufficient to ensure fluidization of the solid. The fatty acids and esters have high boiling points and so it may be advantageous to inject these reactants still in liquid form directly into the fluidized bed of solid, with contact with the hot catalyst ensuring rapid evaporation of the reactants, and also an increase in the gas volume ensuring fluidization. The temperature of the reactor is regulated partly by the entry of liquid and gaseous reactants at a high temperature, and partly by spines for circulation of a heat transfer fluid that are installed actually within the reactor.

Metathesis Step

Metathesis reactions have been known for a long time, although their industrial applications are relatively limited. With regard to their use in the conversion of fatty acids (esters), reference may be made to the article by J. C. Mol "Catalytic metathesis of unsaturated fatty acid esters and oil" in Topics in Catalysis, vol. 27, Nos. 1-4, February 2004, p. 97 (Plenum Publishing).

Catalysis of the metathesis reaction has been the subject of a great many studies and the development of sophisticated catalyst systems. Mention may be made, for example, of the tungsten complexes developed by Schrock et al. (J. Am. Chem. Soc. 108 (1986) 2771 or Basset et al. Angew. Chem., Ed. Engl. 31 (1992) 628. Having appeared more recently are catalysts known as Grubbs catalysts (Grubbs et al., Angew. Chem., Ed. Engl. 34 (1995) 2039 and Organic Lett. 1 (1999) 953), which are ruthenium-benzylidene complexes. This is a homogeneous catalysis. Heterogeneous catalysts have also been developed, based on metals such as rhenium, molybdenum, and tungsten that are deposited on alumina or silica.

Finally, studies have been carried out for the production of immobilized catalysts, these being catalysts whose active principle is that of the homogeneous catalyst, especially the ruthenium-carbene complexes, but is immobilized on an inert support. The objective of three studies is to enhance the selectivity of the cross metathesis reaction with regard to side-reactions, such as the "homo-metatheses" between the reactants when combined. The studies relate not only to the structure of the catalysts but also to the effect of the reaction medium and to the additives that may be introduced. They also relate to the methods of recovering the catalyst after reaction.

In the process of embodiments of the disclosure, any active and selective metathesis catalyst will be able to be used. Preferably, however, ruthenium-based catalysts will be used.

The cross metathesis reaction with the acrylate compound is carried out under very well-known conditions. The reaction temperature is between 20 and 100° C., generally at atmospheric pressure, in a stream of inert gas or under partial vacuum, to allow easy release of ethylene in the presence of a ruthenium-based catalyst.

The ruthenium catalysts are selected preferably from charged or noncharged catalysts of general formula:

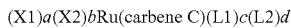

(X1)$a$(X2)$b$Ru(carbene C)(L1)$c$(L2)$d$ in which:
- a, b, c, and d are integers, with a and b being 0, 1 or 2; c and d being 0, 1, 2, 3, or 4,
- X1 and X2, which are identical or different, each represent a charged or noncharged unidentate or multidentate ligand; examples include halides, sulfate, carbonate, carboxylates, alkoxides, phenoxides, amides, tosylate, hexafluorophosphate, tetrafluoroborate, bis-triflylamide, tetraphenylborate, and derivatives.
- X1 or X2 may be bonded to L1 or L2 or to the (carbene C) so as to form a bidentate (or chelate) ligand on the ruthenium, and
- L1 and L2, which are identical or different, are electron-donating ligands such as phosphine, phosphite, phosphonite, phosphinite, arsine, stilbine, an olefin or an aromatic, a carbonyl compound, an ether, an alcohol, an amine, a pyridine or derivative, an imine, a thioether, or a heterocyclic carbene,
- L1 or L2 may be bonded to the (carbene C) so as to form a bidentate or chelate ligand,
   - The (carbene C) may be represented by the general formula: C_(R1)_(R2), for which R1 and R2 are identical or different, such as hydrogen or any other saturated or unsaturated cyclic, branched, or linear hydrocarbon group, or aromatic hydrocarbon group. Examples include complexes of ruthenium with alkylidenes, or with cumulenes such as vinylidenes Ru=C=CHR, or with allenylidenes Ru=C=C=CR1R2, or with indenylidenes.

A functional group which enhances the retention of the ruthenium complex in the ionic liquid may be grafted on at least one of the ligands X1, X2, L1, L2, or on the carbene C. This functional group may be charged or noncharged, such as, preferably, an ester, an ether, a thiol, an acid, an alcohol, an amine, a nitrogen-containing heterocycle, a sulfonate, a carboxylate, a quaternary ammonium, a guanidinium, a quaternary phosphonium, a pyridinium, an imidazolium, a morpholinium, or a sulfonium.

Hydrogenation Step

The step of synthesizing ω-amino esters or ω-amino fatty acids from unsaturated fatty (acid) nitrile-esters involves a conventional hydrogenation referred to in the Encyclopedias mentioned above, in the same sections and chapters. Hydrogenation of the nitrile function automatically entails saturation of the double bond present in the molecule.

The reduction of the nitrile function to primary amine is well known to the skilled person. The hydrogenation may be carried out in the presence of precious metals (Pt, Pd, Rh, Ru, etc.) at a temperature of between 20 and 100° C. under a pressure of 1 to 5 bar. It may also be carried out in the presence of catalysts based on iron, nickel, or cobalt, which may entail more severe conditions, with temperatures of the order of 150° C. and with high pressures of several tens of bar. The catalysts are numerous, but preference is given to using Raney nickels and Raney cobalts. In order to promote the formation of primary amine, a partial pressure of ammonia is employed.

With preference, the step of reducing fatty (acid) nitrile-esters to ω-amino esters or ω-amino fatty acids involves a hydrogenation using any conventional catalyst and preferably Raney nickels and Raney cobalts.

The charge treated is preferably in the form of ω-unsaturated fatty acid ester.

The Process of Embodiments of the Disclosure is Illustrated by the Examples which Follow, which are Given without Limitation Example 1

Nitrilation

The active element of the catalyst that is used is an Anatase ST 31119 titanium oxide produced by the company Saint-Gobain, having a specific surface area of 48 m$^2$/g. The titanium oxide is impregnated with an ammonium paratungstate solution to give a homogeneous coating of tungsten oxide of 5% by weight. The solid is subsequently calcined in a stream of air at 400° C. for 2 hours.

1 g of catalyst is placed in a tubular reactor with a diameter of 10 mm. Silicon carbide is placed over the catalyst bed, and ensures preheating of the reactants. The reactor is supplied with a gas mixture of ammonia and methyl undecylenate, in a molar ratio of 5/1 and with a HSV of 600 h$^{-1}$, or a contact time of approximately 5 seconds. The reactants are preheated very rapidly to 250° C. before entering the reactor. Following reaction, the gases are cooled to approximately 120° C., to allow condensation of the nitrile, and of unconverted reactants, and to keep the ammonia and also the water and methanol produced in the gas phase. The products of the reaction are subsequently analyzed by chromatography.

The conversion of the methyl undecylenate is 99.5%, and the yield of nitrile is 96%, at a reaction temperature of 300° C. The selectivity for 10-cyanodecene (omega unsaturated nitrile) is 95%, relative to the entirety of the nitriles produced.

Example 2

Comparative

This example illustrates the conventional liquid-phase nitrilation step converting 10-undecenoic acid into nitrile of formula CN—(CH$_2$)$_8$—CH=CH$_2$.

The nitrilation reaction of 10-undecenoic acid (3.5 g) to form the ω-unsaturated nitrile of formula CN—(CH$_2$)$_8$—CH=CH$_2$ is carried out batchwise. The reaction mixture is heated to 160° C. at a rate of 1° C. per minute. Introduction of ammonia (0.417 liter/kg acid·min) commences when the 160° C. have been reached stably, and this temperature is maintained until the acid index of the mixture falls below 0.1 mg KOH/g. The temperature is subsequently increased to 265° C. (the temperature is limited by the very substantial evaporation of the mixture at the operating pressure). The reaction is halted after 18 hours. Through the synthesis, a dephlegmator located downstream of the reactor is maintained at 130° C. The reaction is carried out at atmospheric pressure in the presence of a zinc oxide catalyst (0.0625% by weight relative to the acid). Continuous removal of the water formed entrains the excess ammonia and allows rapid completion of the reaction. 2.6 g of the nitrile are recovered, and are separated by vacuum distillation. The omega unsaturated nitrile represents 90% of the nitriles obtained.

Example 3

Cross Metathesis

This example illustrates the cross metathesis reaction of undecenenitrile of formula CN—(CH$_2$)$_8$—CH═CH$_2$ with methyl acrylate, with the Hoveyda-Grubbs II catalyst:

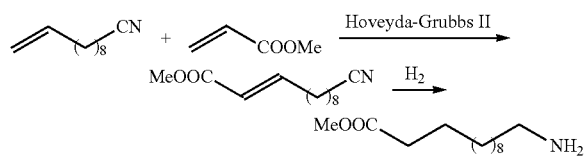

A 50 ml Schlenk tube purged with nitrogen is charged with 83 mg of 10-undecenenitrile (0.5 mmol), 86 mg of methyl acrylate (1 mmol) and 10 ml of toluene distilled over sodium benzophenone. 9.5 mg of 2nd-generation Hoveyda-Grubbs catalyst (1.5×10$^{-2}$ mmol) are added, and the mixture is heated at 100° C. for 1 hour.

Analysis by gas chromatography shows that the conversion of 10-undecenitrile is 100% and that the yield of usaturated nitrile-ester is 98%.

Example 4

Hydrogenation

The reaction mixture obtained from example 3 is then transferred to a 50 ml Parr bomb (filled to 22 ml). 10 mg of 1% Pd/C catalyst and 17 mg of potassium tert-butoxide (0.15 mmol) are added and the bomb is pressurized under 20 bar of hydrogen. Heating is carried out at 80° C. for 48 hours with magnetic stirring.

Analysis by gas chromatography shows that the conversion of the unsaturated nitrile-ester is 90% and that the yield of methyl 12-amino-dodecanoate is 64%.

Example 5

Comparative

This example illustrates the step of conventional liquid-phase nitrilation converting the methyl ester of 10-undecenoic acid into nitrile of formula CN—(CH$_2$)$_8$—CH═CH$_2$.

The nitrilation reaction of the ester of 10-undecenoic acid (3.77 g) to form the ω-unsaturated nitrile of formula CN—(CH$_2$)$_8$—CH═CH$_2$ is carried out batchwise, and in liquid phase. The procedure is as for example 2. The reaction mixture is heated to 160° C. at a rate of 1° C. per minute. Introduction of ammonia (0.417 liter/kg acid·min) commences when the 160° C. have been reached stably. The acid index remains low since an ester is present. The temperature is subsequently raised to 240° C. (the temperature is limited by the boiling point of the methyl ester). The reaction is carried out with total reflux of the methyl ester and is therefore very difficult to carry out, and energy-consuming. The reaction temperature increases gradually with the conversion of the methyl ester, reaching a plateau due to the boiling of the desired product: 10-undecenenitrile. The reaction is halted after 18 hours. Throughout the synthesis, a dephlegmator located downstream of the reactor is maintained at 130° C. The reaction is carried out at atmospheric pressure in the presence of a zinc oxide catalyst (0.0625% by weight relative to the acid). Continuous removal of the water formed entrains the excess ammonia and allows rapid completion of the reaction. 1.2 g of the nitrile are recovered, and are separated by vacuum distillation. The omega unsaturated nitrile represents 85% of the nitriles obtained.

Example 6

Nitrilation

Nb$_2$O$_5$, freshly prepared by hydrolysis of niobium chloride (until chloride is absent from the washing liquors in the silver nitrate test), then calcining at 300° C. in air for 1 hour, is used as catalyst.

5 g of catalyst are placed in a tubular reactor with a diameter of 10 mm. Silicon carbide is placed over the catalyst bed, and ensures preheating of the reactants. The reactor is supplied with a gas mixture of ammonia and methyl undecylenate, in a molar ratio of 5/1 and with a HSV of 120 h$^{-1}$, or a contact time of approximately 30 seconds. The reactants are preheated very rapidly to 200° C. before entering the reactor. Following reaction, the gases are cooled to approximately 120° C., to allow condensation of the nitrile, and of unconverted reactants, and to keep the ammonia and also the water and methanol produced in the gas phase. The products of the reaction are subsequently analyzed by chromatography.

The conversion of the methyl undecylenate is 97%, and the yield of nitrile is 95%, at a reaction temperature of 250° C. The selectivity for 10-cyanodecene or 10-undecenenitrile (omega unsaturated nitrile) is 96%, relative to the entirety of the nitriles produced.

The invention claimed is:

1. A process for synthesizing acids or esters of ω-aminoalkanoic acids comprising 11 or 12 carbon atoms from ω-unsaturated acid or ester comprising, respectively, 10 or 11 carbon atoms, wherein the process comprises:
   nitrilation of the ω-unsaturated acid/ester of the charge, of formula CH$_2$═CH—(CH$_2$)$_n$—COOR, in which n is 7 or 8 and R is either H or an alkyl radical comprising 1 to 4 carbon atoms, by action of ammonia, in a reactor operating continuously in gas phase or in mixed gas-liquid phase, in the presence of a solid catalyst,
   conversion of the resulting nitrile of formula CH$_2$═CH—(CH$_2$)$_n$—CN by metathesis with an acrylate of formula CH$_2$═CH—COOR$_1$, where R$_1$ is either H or an alkyl radical comprising 1 to 4 carbon atoms, and
   hydrogenative reduction of the nitrile function of the compound of formula R$_1$OOC—CH═CH—(CH$_2$)$_n$—CN to give an amino acid or an amino ester of formula R$_1$OOC—(CH$_2$)$_{n+2}$—CH$_2$NH$_2$.

2. The process as claimed in claim 1, wherein, in the nitrilation step performed in gas phase, the ω-unsaturated fatty acid ester is evaporated and brought at a temperature of between 180 and 350° C. into contact with ammonia introduced at a temperature of between 150 and 600° C. and under a pressure of between 0.1 and 10 atmospheres (absolute), in the presence of the solid catalyst.

3. The process as claimed in claim 2, wherein the reaction temperature is generally between 200 and 400° C., and wherein the rates at which the reactants are introduced are such that the contact time with the solid catalyst is between 1 second and 300 seconds.

4. The process as claimed in claim 1, wherein the step of nitrilation of the ω-unsaturated fatty acid ester is carried out in mixed phase according to the trickle bed technique, with the optionally preheated w-unsaturated fatty acid ester being conveyed progressively in trickling liquid form over the solid catalyst heated at a temperature such that there is partial, progressive evaporation of the ester, permitting the reactions with ammonia on contact with the surface of the catalyst or in its immediate proximity.

5. The process as claimed in claim 4, wherein the reaction temperature is generally between 200 and 400° C., and in that the rate at which the ester is introduced is such that the mean residence time of the liquid phase in the reactor is less than 1 hour.

6. The process as claimed in claim 1, wherein the molar $NH_3$/fatty ester ratio of the reactants is between 1 and 50.

7. The process as claimed in claim 1, wherein the solid catalyst is selected from the class of metal oxides consisting of the oxides of metals, alone or in a mixture.

8. The process as claimed in claim 7, wherein the oxides or mixed oxides that constitute the catalyst may be doped with other metals, the dopants suitable for application including the following: rare earths, La, Pr, Nd, Sm, Eu, Dy, Gd, Ho, Yb, and also Cu, Ni, Fe, Pb, Sn, In, Mn, Co, Mo, W, Nb, Zn, Cr, Si, Mg, Ca, Sr, Sc, and Y.

9. The process as claimed in claim 7, wherein the catalysts have a specific surface area between 10 and 500 $m^2/g$.

10. The process as claimed in claim 1, wherein the cross metathesis reaction with the acrylate compound is carried out at a temperature of between 20 and 100° C., generally at atmospheric pressure, to allow release of ethylene, in the presence of a ruthenium-based catalyst.

11. The process as claimed in claim 1, wherein the ruthenium catalysts are selected from charged or noncharged catalysts of general formula:

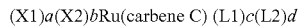

$(X1)_a(X2)_b Ru(\text{carbene C})(L1)_c(L2)_d$ in which:
- a, b, c, and d are integers, with a and b being 0, 1 or 2; c and d being 0, 1, 2, 3, or 4,
- X1 and X2, which are identical or different, each represent a charged or noncharged unidentate or multidentate ligand,
- X1 or X2 are bonded to L1 or L2 or to the (carbene C) so as to form a bidentate (or chelate) ligand on the ruthenium, and
- L1 and L2, which are identical or different, are electron-donating ligands such as phosphine, phosphite, phosphonite, phosphinite, arsine, stilbine, an olefin or an aromatic, a carbonyl compound, an ether, an alcohol, an amine, a pyridine or derivative, an imine, a thioether, or a heterocyclic carbene,
- L1 or L2 are bonded to the (carbene C) so as to form a bidentate or chelate ligand,
- the (carbene C) is represented by the general formula: C_(R1)_(R2), for which R1 and R2 are identical or different, such as hydrogen or any other saturated or unsaturated cyclic, branched, or linear hydrocarbon group, or aromatic hydrocarbon group.

12. The process as claimed in claim 1, wherein the step of reduction of the fatty (acid) nitrile esters to ω-amino esters or ω-amino-fatty acids involves a hydrogenation using any conventional catalyst.

13. The process as claimed in claim 1, wherein the treated charge is in the form of an ω-unsaturated fatty acid ester.

* * * * *